United States Patent [19]

Hartman et al.

[11] Patent Number: 4,914,111

[45] Date of Patent: Apr. 3, 1990

[54] 4-BENZYLTHIOPHENE (OR FURAN)-2-SULFONAMIDES AS ANTIGLAUCOMA AGENTS

[75] Inventors: George D. Hartman, Lansdale; Wasyl Halczenko, Hatfield, both of Pa.

[73] Assignee: Merck & Co., Inc., Rahway, N.J.

[21] Appl. No.: 28,825

[22] Filed: Mar. 23, 1987

[51] Int. Cl.$^4$ .................. A61K 31/38; A61K 31/34; C07D 333/32; C07D 307/02
[52] U.S. Cl. ........................... 514/326; 514/422; 514/445; 514/471; 514/473; 549/62; 549/65; 549/66; 549/479; 546/212; 546/213; 548/527
[58] Field of Search ............... 549/65, 62, 66; 514/326, 422, 445, 471, 473; 546/212, 213; 548/527

[56] References Cited

U.S. PATENT DOCUMENTS

| | | | |
|---|---|---|---|
| 4,386,098 | 5/1983 | Woltersdorf, Jr. et al. | 424/270 |
| 4,416,890 | 11/1983 | Woltersdorf, Jr. | 424/270 |
| 4,426,388 | 1/1984 | Woltersdorf, Jr. | 424/270 |
| 4,477,466 | 10/1984 | Shepard | 424/275 |
| 4,486,444 | 12/1984 | Shepard | 424/275 |
| 4,542,152 | 9/1985 | Shepard | 514/445 |
| 4,544,667 | 10/1985 | Shepard et al. | 514/470 |
| 4,585,787 | 4/1986 | Shepard | 514/445 |
| 4,665,090 | 5/1987 | Graham | 549/65 |

Primary Examiner—Alan Siegel
Attorney, Agent, or Firm—William H. Nicholson; Joseph F. DiPrima; Edward W. Murray

[57] ABSTRACT

Thiophene (or furan)-2-sulfonamides with a 4-benzyl substituent are effective in the treatment of elevated intraocular pressure and glaucoma following topical ocular administration.

6 Claims, No Drawings

4-BENZYLTHIOPHENE (OR FURAN)-2-SULFONAMIDES AS ANTIGLAUCOMA AGENTS

SUMMARY OF THE INVENTION

This invention is concerned with a genus of novel compounds with structural formula:

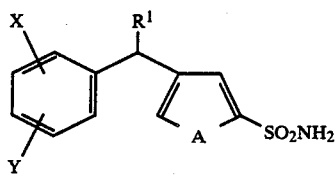

wherein the variable substituents are as defined below, which are useful in the treatment of elevated intraocular pressure and glaucoma by topical ocular administration.

The invention is also concerned with ophthalmic formulations comprising one or more of the novel compounds as active ingredients either alone or in combination with other ophthalmic agents.

The invention is also concerned with the use of the novel compounds or ophthalmic formulations thereof in the treatment of elevated intraocular pressure and glaucoma.

Finally, the invention is concerned with processes for preparing the novel compounds.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

Additionally, U.S. Pat. 4,544,667 discloses a series of benzofuran-2-sulfonamides, and U.S. Pat. Nos. 4,477,466; 4,486,444; 4,542,152; and 4,585,787 disclose 5-phenylsulfonylthiophene-2-sulfonamides and 5-benzoylthiophene-2-sulfonamides and alkanoyloxy derivatives thereof which are topically effective carbonic anhydrose inhibitors useful in the treatment of elevated intraocular pressure and glaucoma.

DETAILED DESCRIPTION OF THE INVENTION

The novel compounds of this invention have general structural formula:

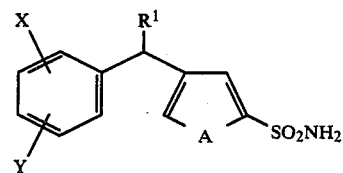

or an ophthalmologically acceptable salt thereof, wherein
A is —S— or —O—;
$R^1$ is hydrogen or —$NHR^2$, wherein,
$R^2$ is
  a) hydrogen,
  b) $C_{1-6}$ alkyl, either straight or branched chain and either unsubstituted or substituted with one or more of
    1) phenyl,
    2) $C_{3-6}$ cycloalkyl; and
X and Y are independently
  a) hydrogen,
  b) $C_{1-6}$ alkyl,
  c) $C_{1-6}$ alkoxy,
  d) hydroxy,
  e) halo such as fluoro, chloro or bromo,
  f) —$(CH_2)_nNH^2R^3$ wherein n is 0–3; $R^2$ is as previously defined and $R^3$ is hydrogen or $C_{1-3}$ alkyl; and if both $R^2$ and $R^3$ are lower alkyl, they can be joined together to form, with the nitrogen to which they are attached, a 5- or 6-membered heterocycle such as pyrrolidine, piperidine, morpholine, thiomorpholine, or the like.

It is preferred that A be —S—. It is also preferred that $R^1$ be —$NHR^2$. It is further preferred that one of X and Y be hydroxyl.

The novel benzyl compounds ($R^1$=H) are prepared by reduction of the corresponding benzoyl compounds first with NaBH₄ or equivalent reagent to the benzhydrol and then with LiAlH₄ to the benzyl. The borohydride reduction is conducted in a $C_{1-3}$ alkanol, preferably ethanol, at about 10°–30° C., preferably about room temperature, for about 6 to 24 hours. The LiAlH₄ reduction is conducted in an ethereal solvent such as diethyl ether, THF, dimethoxyethane or the like in the presence of an equimolar amount of AlCl₃ at about 0°–30° C. followed by refluxing for about 0.25 to 4 hours.

The novel α-aminobenzyl compounds of this invention are prepared by forming a Schiff's base of an amine and the above benzoyl compounds followed by reduction of this imine with NaBH₄.

The Schiff's base formation is accomplished in an inert solvent such as benzene, toluene, or the like at about 15°–30° C. in the presence titanium tetrachloride over a period of about 1–5 hours. The borohydride reduction is performed as previously described.

Phenolic ethers are deetherified by standard procedures such as 48% HBr, pyridine.HCl, or the like.

For use in treatment of conditions relieved by the inhibition of carbonic anhydrase, the active compound can be administered either systemically, or, in the treatment of the eye, topically. The dose administered can be from as little as 0.1 to 25 mg or more per day, singly, or preferably on a 2 to 4 dose per day regimen.

When administered for the treatment of elevated intraocular pressure or glaucoma, the active compound is most desirably administered topically to the eye, although systemic treatment is also satisfactory.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

When given by the topical route, the active drug or an ophthalmologically acceptable salt thereof is formulated into an ophthalmic preparation.

The active drug of this invention is most suitably administered in the form of ophthalmic pharmaceutical compositions adapted for topical administration to the eye such as a suspension, ointment, gel or as a solid insert. Formulations of these compounds may contain from 0.01 to 15% and especially 0.5% to 2% of medicament. Higher dosages as, for example, about 10%, or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

These hereinbefore described dosage values are believed accurate for human patients and are based on the known and presently understood pharmacology of the compounds, and the action of other similar entities in the human eye. They reflect the best mode known. As with all medications, dosage requirements are variable and must be individualized on the basis of the disease and the response of the patient.

The thrust of this invention as hereinbefore stated is to provide an ocular antihypertensive agent for the eye, both human and animal, that acts by inhibiting carbonic anhydrase and, thereby, impeding the formation of aqueous humor.

EXAMPLE 1

4-(4-Hydroxybenzyl)thiophene-2-sulfonamide

Step A: Preparation of 3-(4-Methoxybenzoyl)thiophene

To 4.0 g (0.0246 m) of 3-bromothiophene in 70 ml ether cooled to −75° C. under N₂ was added dropwise 0.0246 m of n-butyllithium (in hexane) at such a rate that the temperature was < −70° C. After addition was complete the reaction mixture was stirred at −75° C. for 10 minutes and then a solution of 4-methoxybenzonitrile (3.46 g, 0.026 m) in 20 ml ether was added dropwise at < −70° C. The resulting suspension was stirred at −75° C. for 45 minutes and then allowed to warm to −10° C. over 2 hours. The reaction mixture was cooled, quenched with 15 ml H₂O and then with 40 ml of 2N HCl. The phases were separated and the aqueous extract was washed with 50 ml ether, and then heated at reflux for 2 hours. This solution was cooled and extracted with 2×60 ml ether. The organic phases were washed with brine, dried and evaporated to give an oil which was triturated with petroleum ether to give the product as a solid, m.p. 58°–61° C.

Step B: Preparation of 4-(4-Methoxybenzoyl)thiophene-2-sulfonic acid 9.7 g (0.05 mol) of product from Step A was dissolved in 75 ml CH₂Cl₂ and cooled to −10° C. Then, 15.3 g (0.15 mol) acetic anhydride was added dropwise followed by the dropwise addition of 5.9 g (0.06 mol) concentrated sulfuric acid. The resulting mixture was stirred at room temperature overnight.

The yellow solid was collected on a filter, washed with CH₂Cl₂ and air dried to provide the desired product.

Step C: Preparation of 4-(4-Methoxybenzoyl)thiophene-2-sulfonamide

To 2.98 g (0.01 mol) of product from Step B suspended in 75 ml CH₂Cl₂ was added excess thionyl chloride and the resulting suspension was stirred, and heated at reflux for 1.5 hours to give a homogeneous solution. The thionyl chloride was evaporated and the residue was extracted with CHCl₃ after ice had been added. The organic extract was washed with brine, dried and the solvent evaporated to give a yellow oil. This was taken up in acetone and treated with 5 ml of concentrated NH₄OH dropwise. After stirring for 15 minutes, this was extracted with chloroform and the extract was dried. Filtration and evaporation of the solvent gave the desired product as a yellow solid, m.p. 173°–175° C.

Step D: Preparation of 4-(4-Methoxybenzhydrol)-thiophene-2-sulfonamide

To 2.97 g (0.01 mol) 4-(4-methoxybenzoyl)-thiophene-2-sulfonamide suspended in 5 ml absolute ethanol at room temperature was added 0.38 g (0.01 mol) sodium borohydride and the resulting mixture was stirred overnight. The solvent was removed in vacuo dried and the residue taken up in 15 ml H₂O, and acidified with 6N HCl and the resulting solution was extracted with ether. The organic extracts were combined, and the solvent removed in vacuo to give a residue that was purified by flash chromatography on silica gel eluting with 1:1 hexane/ethyl acetate to give pure product as a viscous oil (Rf 0.5).

Step E: Preparation of 4-(4-Methoxybenzyl)thiophene-2-sulfonamide

To a solution of 1.14 g (0.03 mol) lithium aluminum hydride in 50 ml ether at 0°–10° C. was added a solution of 4.0 g (0.03 mol) aluminum chloride in 50 ml ether dropwise. A solution of 6.0 g (0.02 mol) of product from the preceding Step in 100 ml ether was added dropwise at room temperature and the resulting mixture was refluxed for 0.5 hour.

The reaction mixture was cooled to 0°–10° C. and quenched with 3N $H_2SO_4$ solution (30 ml), causing a vigorous evolution of gas. The mixture was carefully poured into 100 ml of 2N HCl solution and extracted with ethyl acetate. The combined organic extracts were dried and the solvent removed in vacuo to give a residue that was purified by flash chromatography on silica gel eluting with 30% ethyl acetate/hexane to provide the product as a white solid, m.p. 75°–77° C.

Alternate synthesis of 4-(4-methoxybenzyl)thiophene-2-sulfonamide

To a solution of 0.667 g (0.005 mol) aluminum chloride in 10 ml THF at 0°–10° C. was added a solution of 0.19 g (0.005 mol) lithium aluminum hydride in 10 ml THF dropwise. Then, a solution of 0.6 g (0.002 mol) 4-(4-methoxybenzoyl)thiophene-2-sulfonamide in 10 ml THF was added dropwise and the resulting mixture was heated at 60° C. overnight at which time all starting material was consumed. The cooled reaction mixture was quenched with saturated aqueous sodium potassium tartrate solution and the resulting grey solid was filtered off. The filtrate was dried and the solvent evaporated to give the title compound.

Step F: Preparation of 4-(4-Hydroxybenzyl)thiophene-2-sulfonamide

A solution of 4.5 g (0.016 mol) of product from the preceding Step in 100 ml of 48% HBr was refluxed for 1.5 hours and the resulting mixture was cooled and poured into ice water. This was extracted with ethyl acetate, and the organic extracts were combined, dried and the solvent was removed in vacuo. The resulting oil was purified by flash chromatography on silica gel eluting with 55/45 hexane:ethyl acetate to provide a yellow semi-solid. This was crystallized from ethyl acetate/hexane to provide pure product as a white solid, m.p. 141°–143° C.

Employing the procedure substantially as described in Example 1, Steps A through F but using as starting materials, the X,Y-benzonitriles and 3-bromothiophene or 3-bromofuran depicted in Table I there are produced the 4-(X,Y-benzyl)thiophene (or furan)-2-sulfonamides and intermediates thereto also depicted in Table I in accordance with the following reaction scheme:

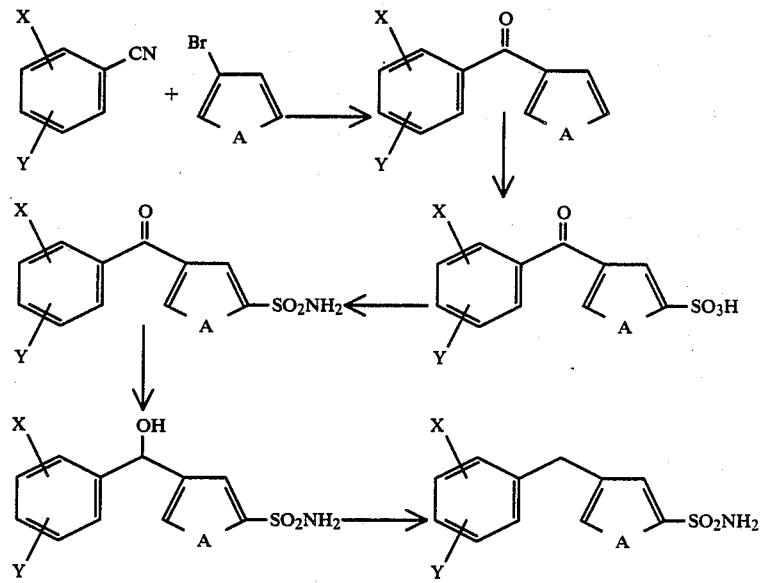

TABLE I

| X | Y | A |
|---|---|---|
| H | 4-OCH$_3$ | —O— |
| H | 4-OH | —O— |
| 3-CH$_3$ | 4-OCH$_3$ | —S— |
| 3-CH$_3$ | 4-OH | —S— |
| H | 4-n-C$_6$H$_{13}$ | —O— |
| H | 4-n-C$_6$H$_{13}$ | —S— |
| 2-F | 4-OCH$_3$ | —S— |
| 2-F | 4-OH | —S— |
| 2-F | 4-OCH$_3$ | —O— |
| 2-F | 4-OH | —O— |
| 3-CH$_2$N(CH$_3$)$_2$ | 4-OH | —S— |
| 3-CH$_2$N(CH$_3$)$_2$ | 4-OH | —O— |

Example 2

4-[(4-Hydroxyphenyl)(methylamino)methyl]thiophene-2-sulfonamide

Step A: Preparation of [4-Methoxyphenyl-4-(thiophene-2-sulfamoyl)]methanone-N-methylimine To a solution of 2.61 g (0.084 mol) methylamine in 175 ml toluene at room temperature was added 5.0 g (0.0168 mol) of 4-(4-methoxybenzoyl)thiophene-2-sulfonamide and the resulting suspension was stirred vigorously in ice as 3.19 g (0.168 mol) titanium tetrachloride was added dropwise. The resulting brownish suspension was stirred at room temperature for 2.5 hours and then poured into ice water. This was extracted with ethyl acetate and the organic extract was dried, filtered through filter aid and the solvent was removed in vacuo to give the product as a tan solid, $R_f$ 0.2 on silica gel eluted with 1:1 ethyl acetate/hexane.

Step B: Preparation of 4-[(4-Methoxyphenyl) (methylamino) methyl]thiophene-2-sulfonamide To 3.90 g (0.01 moles) of product from Step A suspended in 100 ml ethanol and cooled to 0°–10° C. was added 1.90 g (0.05 mol) sodium borohydride portionwise and the resulting suspension was stirred at room temperature for 2.0 hours. The reaction mixture was cooled, made acidic with 6N HCl solution and the solvent was evaporated. The resulting solid was taken up in 75 ml H₂O and extracted with ethyl acetate. The organic extract was dried and the solvent removed in vacuo to give a solid that was triturated with chloroform to give a solid residue. This was recrystallized from isopropanol to provide pure product, $R_f$ 0.4 on silica gel eluted with 10% methanol/chloroform, m.p. 155°–156° C.

Step C: Preparation of 4-[(4-Hydroxyphenyl) (methylamino) methyl]-2-thiophenesulfonamide A solution of 1.0 g (0.0032 mol) product from Step B in 30 ml 48% aqueous hydrobromic acid was heated at 85° C. for 4.0 hours. The cooled reaction mixture was made alkaline with concentrated NH₄OH solution and was extracted with ether. The organic extract was dried, the solvent evaporated and the resulting residue was purified by flash chromatography on silican gel eluting with 21 % methanol/chloroform to give pure product as a tan solid, m.p. 127°–129° C.

Employing the procedure substantially as described in Example 2, but using as starting materials the X,Y-benzoylthiophene (or furan)-2-sulfonamides and the amines depicted in Table II there are prepared th α-aminobenzyl compounds also depicted in Table II in accordance with the following reaction scheme:

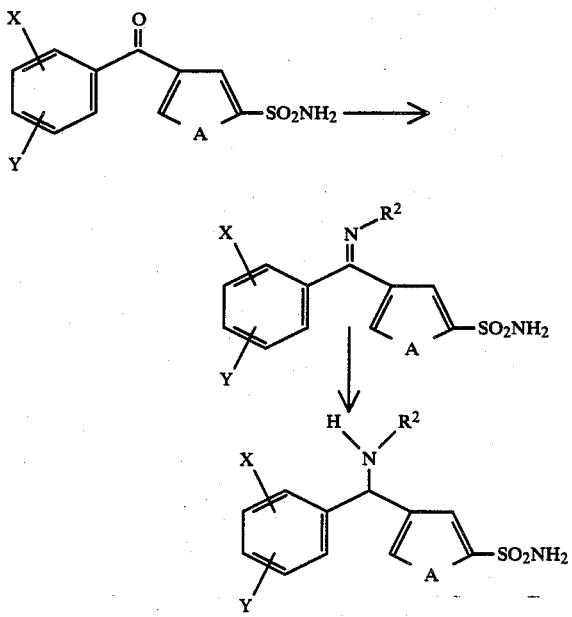

TABLE II

| X | Y | A | R² |
|---|---|---|---|
| H | 4-OCH₃ | —S— | —C₄H₉-i (oil) |

TABLE II-continued

| X | Y | A | R² |
|---|---|---|---|
| H | 4-OH | —S— | —C₄H₉-i |
| 3-CH₃ | 4-OCH₃ | —S— | —CH₂C₆H₅ |
| 3-CH₃ | 4-OH | —S— | —CH₂C₆H₅ |
| H | 4-n-C₆H₁₃ | —O— | —CH₂— |
| H | 4-n-C₆H₁₃ | —S— | —CH₂— |
| 2-F | 4-OCH₃ | —S— | —C₃H₇-i |
| 2-F | 4-OH | —S— | —CH₃-i |
| 2-F | 4-OCH₃ | —O— | —CH₃ |
| 2-F | 4-OH | —O— | —CH₃ |
| 3-CH₂N(CH₃)₂ | 4-OH | —S— | —C₄H₉-i |
| 3-CH₂N(CH₃)₂ | 4-OH | —O— | —C₄H₉-i |
| H | 4-OCH₃ | —O— | —C₄H₉-i |
| H | 4-OH | —O— | —C₄H₉-i |

EXAMPLE 3

| Solution Composition | | |
|---|---|---|
| 4-(4-Hydroxybenzyl)thiophene-2-sulfonamide | 1 mg | 15 mg |
| Monobasic sodium phosphate .2 H₂O | 9.38 mg | 6.10 mg |
| Dibasic sodium phosphate .12 H₂O | 28.48 mg | 16.80 mg |
| Benzalkonium chloride | 0.10 mg | 0.10 mg |
| Water for injection q.s. ad. | 1.0 ml | 1.0 ml |

The sterile components are added to and suspended in sterile water. The pH of the suspension is adjusted to 6.8 sterilely and diluted to volume.

EXAMPLE 4

| | |
|---|---|
| 4-(4-Hydroxybenzyl)thiophene-2-sulfonamide | 5 mg |
| petrolatum q.s. ad. | 1 gram |

Compound I and the petrolatum are aseptically combined.

EXAMPLE 5

| | |
|---|---|
| 4-(4-Hydroxybenzyl)thiophene-2-sulfonamide | 1 mg |
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserted are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 6

| | |
|---|---|
| 4-(4-Hydroxybenzyl)thiophene-2-sulfonamide | 1 mg |
| Hydroxypropyl cellulose q.s. ad. | 12 mg |

Ophthalmic inserted are manufactured from a solvent cast film prepared by making a viscous solution of the powdered ingredients listed above using methanol as the solvent. The solution is placed on a Teflon plate and

What is claimed is:

1. A compound of structural formula:

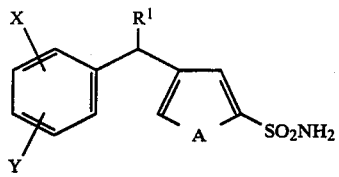

or an ophthalmologically acceptable salt thereof wherein:

A is —S— or —O—;

$R^1$ is hydrogen or —$NHR^2$ wherein $R^2$ is hydrogen or $C_{1-6}$ alkyl, either straight or branched chain, and either unsubstituted or substituted with one or more of phenyl or $C_{3-6}$ cycloalkyl; and X and Y are independently:
a) hydrogen,
b) $C_{1-6}$ alkyl,
c) $C_{1-6}$ alkoxy,
d) hydroxy,
e) halo, or
f) —$(CH_2)_nNR^2R^3$, wherein n is 0, 3; $R^2$ is as previously defined and $R^3$ is hydrogen or $C_{1-3}$ alkyl; and if both $R^2$ and $R^3$ are lower alkyl, they can be joined together to form, with the nitrogen to which they are attached, a 5-, or 6-membered heterocycle.

2. The compound of claim 1, wherein A is —S—.

3. The compound of claim 2, wherein $R^1$ is —$NHR^2$.

4. The compound of claim 3, wherein one of X and Y is —OH.

5. An ophthalmological composition for the treatment of elevated intraocular pressure and glaucoma comprising an ophthalmogical carrier and an effective intraocular pressure lowering and antiglaucoma amount of the compound of claim 1.

6. A method of treating elevated intraocular pressure and glaucoma which comprises the topical ocular administration to a patient in need of such treatment of an effective intraocular pressure lowering and antiglaucoma amount of the Compound of claim 1.

* * * * *